United States Patent [19] [11] 4,160,785
Webb et al. [45] Jul. 10, 1979

[54] REDUCTION OF DIIMINO COMPOUNDS TO DIAMINO COMPOUNDS

[75] Inventors: Jimmy L. Webb, Ballston Lake, N.Y.; John E. Corn, Mt. Vernon, Ind.

[73] Assignee: General Electric Company, Schenectady, N.Y.

[21] Appl. No.: 701,517

[22] Filed: Jul. 1, 1976

Related U.S. Application Data

[63] Continuation-in-part of Ser. No. 544,139, Jan. 27, 1975, abandoned.

[51] Int. Cl.$^2$ .............................................. C07C 85/08
[52] U.S. Cl. .................................................. 260/583 P
[58] Field of Search ........... 260/585 C, 566 R, 583 P, 260/563 D, 566 F, 583 R

[56] References Cited

U.S. PATENT DOCUMENTS

| | | | |
|---|---|---|---|
| 2,636,051 | 4/1953 | Whetstone et al. | 260/584 A |
| 3,652,672 | 3/1972 | Kliegman et al. | 260/566 R |

*Primary Examiner*—Winston A. Douglas
*Assistant Examiner*—John Doll
*Attorney, Agent, or Firm*—Joseph T. Cohen; Charles T. Watts

[57] ABSTRACT

Organic diamines can be prepared by hydrogenating a preformed diimine in the presence of methanol and in the further presence of the tertiary alkyl mono-amine used to make the diimino compound. The diamino compounds thus obtained are useful as catalysts in the preparation of polyphenylene oxide resins.

4 Claims, No Drawings

REDUCTION OF DIIMINO COMPOUNDS TO DIAMINO COMPOUNDS

This application is a continuation-in-part of application Ser. No. 544,139, filed Jan. 27, 1975, now abandoned and assigned to the same assignee as the present invention.

This invention is concerned with a process for preparing organic amino compounds. More particularly, the invention relates to a process which comprises hydrogenating in the presence of a hydrogenation catalyst used for this purpose, the preformed diimino reaction product of glyoxal with a tertiary alkyl mono-amino compound corresponding to the formula $$R\text{—}NH_2 \qquad (I)$$

thereby to form the imino compound of the formula $$R\text{—}N\overset{H}{=}C\text{—}C\overset{H}{=}N\text{—}R \qquad II$$

in the further presence of methanol and the aforesaid mono-amine to form a diamino compound of the formula $$R\text{—}\overset{H}{N}\text{—}CH_2\text{—}CH_2\text{—}\overset{H}{N}\text{—}R \qquad III$$

where R is a monovalent alkyl hydrocarbon radical of from 4 to 10 carbon atoms containing a $$\begin{array}{c} R' \\ | \\ -C- \\ | \\ R' \end{array} \qquad IV$$

grouping connected directly to the nitrogen atom of either the amino compound or imino compound, where R' is $CH_3$—, or $C_2H_5$—, or mixtures of the same.

The condensation of glyoxal with an amine to yield diimines is known in the literature as shown in the following equation $$R\text{—}NH_2 + H\overset{O}{\underset{\|}{C}}\text{—}\overset{O}{\underset{\|}{C}}\text{—}H \longrightarrow R\text{—}N\overset{H}{=}C\text{—}C\overset{H}{=}N\text{—}R$$

where R has the meaning given above [see article by J. M. Kliegman and R. K. Barnes, "Conjugated Aliphatic Diimines from Glyoxal and Aliphatic Primary Amines," in Tetrahedron 26, pages 2555–2560 (1970)]. However, to our knowledge, no example of the reduction of diimines to diamines has been disclosed in the literature whereby conservation of the mono-amine is adequately considered.

Unexpectedly, we have discovered that we can form tertiary alkyl diamines readily and in good yield by first reacting glyoxal with a mono-amino compound of the general formula I to form a diimino compound of formula II, and then reducing the diimino compound with hydrogen in the presence of a usual hydrogenation catalyst under the conditions recited above to form a diamino compound of formula III.

In preparing the diimino compound, the tertiary alkyl mono-amino compound, dissolved in water or dissolved in a water-soluble solvent, such as methanol, ethanol, tetrahydrofuran, etc., is mixed with the glyoxal which is advantageously in the form of an aqueous solution. The concentration of the water with the mono-amine or of the water-soluble solvent with the mono-amine can be varied widely and need only be sufficient to effect an intimate solution of the reactants. As far as the aqueous glyoxal solution is concerned, generally concentrations of from 20 to 80% glyoxal based on the total weight of the glyoxal and water are adequate for the purpose.

Usually, it is only necessary to mix adequately the aqueous glyoxal solution with the tertiary mono-amine to form the desired imino compound. Slight heating of the mixture, for instance, from about 25° to 50° C. or even higher can be advantageously employed if desired, but ordinarily this is not critical, and may not be necessary especially since there is a slight exotherm occurring upon mixing. The imino compound thus obtained is isolated and purified by usual means to give the corresponding diimine in the preformed state.

The diimine is then advantageously dissolved in a suitable solvent and any one of usual hydrogenation catalysts employed in the art for reduction reactions is used to cause reduction of the diimine to the diamine by the introduction of hydrogen. Suitable solvents which can be used for dissolving the diimine for reaction during the reduction process can be, for instance, methanol, ethanol, etc. Methanol is especially effective for the purpose. The concentration of the diimine in the solvent is not critical and can vary from about 10 to 25%, by weight, or more, based on the weight of the latter and the solvent, the important thing being that the solution of the diimine is employed in a convenient form.

Thereafter, any well-known hydrogen reduction catalyst normally employed by persons skilled in the art in reduction reactions is added in a small but effective amount as is customary when reducing the usual organic compounds capable of being reduced by hydrogenation. Among such reduction catalysts may be mentioned, for instance, platinum, platinum oxide, rhenium, Raney-nickel, etc. The amount of reduction catalyst employed is not critical, but generally is used within the range of from about 0.2 to about 10%, by weight, or more of the reduction catalyst based on the weight of the diimine. Thereafter, the mixture of ingredients is placed in a pressure reactor vessel, such as a Parr shaker, and at elevated pressures in the order of about 25 to 100 psi or more. Hydrogen is passed into the pressure reactor while continuing to shake the latter. Generally, room (or ambient) temperatures of about 20° to 30° C. are adequate for the reaction to take place although a slight increase in temperature may be desired for acceleration of reaction consistent with the ability of the pressure reactor to withstand the increased pressure generated by the elevated temperatures. After a sufficient time by which it is established that the theoretical amount of hydrogen has been absorbed, the pressure reactor is opened, the catalyst removed by filtration, the solvent removed, for example, by evaporation, preferably under vacuum, to yield a product which upon further purification will give the desired diamine.

One of the unusual discoveries we made is the fact that in preparing the diimine, it is important that one employ an alkyl hydrocarbon containing the tertiary group of formula IV attached to the nitrogen atom. For instance, consistently good yields of the diimine are obtained in the order of about 80 to 95 or more percent by this process. If one employs, for instance, a secondary amine containing the

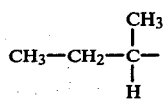

grouping attached directly to the nitrogen atom with the glyoxal, the product yield drops considerably; if one employs a primary amine containing a primary alkyl group attached directly to nitrogen such as the grouping

essentially no yield of diimine is obtained. It is thus clear that hydrogen atoms on the carbon adjacent the nitrogen atom have an unexpected deleterious effect on the yield of diimine.

In order that those skilled in the art may better understand how the present invention may be practiced, the following examples are given by way of illustration and not by way of limitation.

Since many of the diimines and diamines are known in the literature, there is no real problem of identifying the materials which are obtained. The identities of the diimines and the diamines were established by nmr together with the boiling points of the compounds.

One of the unexpected discoveries that we have made is the fact that using lower alkanols, particularly methanol, as the solvent for the diimine during hydrogenation, gave unusually good yields in the reduction step and appeared to be quite superior to any other solvents that were tried. In addition, we also unexpectedly discovered that by including, during the reduction step, a certain amount of the initial tertiary mono-amine used to make the diimine, still better yields of the ultimate diamino compound were obtained. The amount of the parent mono-amine added to the diimino compound during the hydrogentation (reduction) step can be varied but generally should be present in from 0.2 to 4 mols of the former per mol of the diimino compound being reduced.

EXAMPLE 1

To a solution of 20 grams of 30% aqueous glyoxal (0.103 mol) and 40 ml. of distilled water was added a solution of 21 ml. (0.2 mol) t-butylamine in 20 ml. water. A slight exotherm occurred raising the temperature slightly above room temperature and causing an oil to separate upon cooling. The oil crystallized as the reaction mixture cooled and the solid which precipitated was collected, washed with water and vacuum dried to yield 14.0 grams (83.25% yield) of a colorless material having a melting point of 54.5°–56.0° C. Analysis of this compound showed it to be N,N'-di-t-butyl ethylene diimine. 13.4 grams (0.08 mol) of the preformed diimine was dissolved in 200 ml. 95% ethanol containing 0.4 gram of platinum oxide and 0.2 gram of 10% platinum on carbon. This mixture was reduced in a Parr shaker at 50 psi and 25° C. by introducing hydrogen into the reaction vessel. After about 10 minutes of reduction with hydrogen whereby approximately 85% of the theoretical amount of hydrogen had been absorbed, the reaction vessel was opened up, the catalyst removed by filtration and the ethanol evaporated in vacuum to yield a residue which upon isolation and purification resulted in a yield of 8.23 grams (60% of theoretical) of the desired N,N'-di-t-butyl ethylene diamine, b.p. 96° C./34 mm Hg.

EXAMPLE 2

To a nitrogen flushed flask containing 72.5 grams of 40% aqueous glyoxal (0.5 mol) and 72.5 grams of water was added a solution of 87.0 grams (1.0 mol) of 1,1-dimethylpropylamine in 72.5 grams of water. A white precipitate formed and the two solutions were slowly mixed together with no apparent exotherm being noted. After about 50 minutes of mixing, two layers were formed. The product was extracted with 225 ml. benzene, the benzene layer dried over sodium sulfate and evaporated in vacuum to give a product which upon distillation yielded 79.7 grams (80% of theoretical yield) of a colorless diimine having the formula

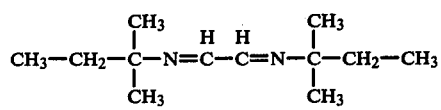

and boiling at 123°–125° C./33 mm Hg. Employing the same conditions for reduction as described in Example 1, the aforesaid diimine of formula V was converted to the corresponding diamine having the formula

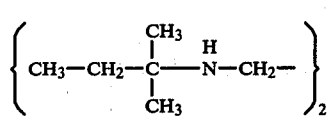

boiling at 113°–115° C. (30 torr).

EXAMPLE 3

In this example, t-butylamine was treated with glyoxal and then reduced similarly as in Example 1, with various exceptions including the use of methanol or ethanol in the reduction step employing hydrogenation catalysts such as platinum oxide or Raney-nickel. The following Table I shows the catalyst concentrations and the use of the aforesaid alkanols and hydrogenation catalysts based on the reduction of N,N'-di-t-butyl ethylene diimine. The conditions of the reaction generally involved 0.1 mol of the isolated diimine in 100 ml. solvent with 100 mg. catalyst rocked in a 250 ml. Parr hydrogenator. The platinum oxide catalyst was used in an amount equal to 100 milligrams, while the Raney-nickel catalyst was used in an amount equal to 5.0 grams. In all instances, the initial hydrogenation pressure was about 54 psi gauge pressure. The initial take up of the hydrogen was determined by extrapolation of the hydrogen rate to time 0. For comparison solvents such as cyclohexane and benzene were also used as the solvents in the reduction step.

TABLE I

| Solvent | Catalyst | Initial $H_2$ Take-up (psi/hr.) | Percent Yield |
|---|---|---|---|
| $CH_3OH$ | PtO | 40.0 | 60 |
| $C_2H_5OH$ | PtO | 6.0 | 64 |
| $CH_3OH$ | Raney-nickel | 6.5 | 60 |
| Cyclohexane | PtO | 0.6 | — |
| Benzene | PtO | 0.4 | — |

From the above, it will be clearly apparent that lower alkanols such as ethanol and especially methanol, have a beneficial effect on the rate of take-up of the hydrogen during the reduction step.

EXAMPLE 4

Employing the same condition as described in Examples 1 to 3, the N,N'-dialkyldiamine having the formula $$(CH_3-C(CH_3)_2-CH_2-C(CH_3)_2-\overset{H}{N}-CH_2-)_2$$

was prepared from the corresponding N,N'dialkyldiimine by first using the glyoxal reaction with the required mono-amine $$CH_3-C(CH_3)_2-CH_2-C(CH_3)_2-NH_2$$

and then reducing the diimine to form the corresponding diamine in the presence of platinum oxide and CH$_3$OH. The properties of the diimino compound and the properties of the corresponding diamine (obtained in a 97% yield) resulting from reduction of the precursor diimino compound are as follows:

| Diimino compound | Diamino compound |
|---|---|
| B.P. 105° C. (1 torr) | B.P. 137°-138° C. (1 torr) |

EXAMPLE 5

The advantage of employing the present starting mono-amine (used to make the successor into compound) during the reduction step of the imino compound is illustrated in the instant example. More particularly, Example 3 was repeated to the point where the N,N'-di-t-butylethylene diimine dissolved in methanol was placed in a Parr hydrogenator together with the corresponding t-butylamine prior to passage of hydrogen into the reactor employing platinum oxide as the hydrogenation catalyst. Hydrogen was passed into the reactor until it was determined that essentially the theoretical amount of hydrogen had been absorbed to form the desired diamino compound. This process was repeated a number of times with the exception that the concentration of the t-butylamine was varied in order to determine the effect of using increased concentration of the parent t-butylamine in the reduction step. The following table shows the improved effect on the yield of the diamine as the result of the addition of the parent mono-amino in varying amounts.

TABLE II

| Moles t-butylamine per mol diimine | % Yield |
|---|---|
| 0 | 60% |
| 0.2 | 83% |
| 0.4 | 85% |
| 0.8 | 87% |
| 1.2 | 88% |
| 2.0 | 91% |

When the above reduction reaction was carried out in the presence of the t-butyl amine but omitting any solvent, no yield of diamine was obtained. Since the parent amine is recovered essentially intact, it can be used repeatedly to effect the increase in yield without any significant cost increment.

It will of course be apparent to those skilled in the art that in addition to the mono-amines employed in the preceding examples wherein R has the generic meaning given above, other mono-amines having from 4 to 10 carbon atoms can be employed without departing from the scope of the invention.

Among the monovalent alkyl hydrocarbons which R can additionally represent wherein the R group has the tertiary carbon atom of formula IV attached to the nitrogen may be mentioned C$_{4-8}$ alkyl groups, for instance, 2-methylbut-2-yl, 2-cyclohexylprop-2-yl, 2-methyl-pent-2-yl, 3-methylpent-3-yl, 2,3-dimethylbut-2-yl, 2-methylhex-2-yl, 3-methylhex-3-yl, 3-methylpent-3-yl, 2,3- and 2,4-dimethylpent-2-yl, 2-methylhept-2-yl, 3-methylhept-3-yl, 3-ethylhex-3-yl, etc. Additional alkyl groups are, for instance, groups of the formulas $$CH_3-(CH_2)_2-\underset{H}{\overset{CH_3}{\underset{|}{C}}}-C(CH_3)_2-$$

$$CH_3-\underset{CH_3}{\overset{CH_3}{\underset{|}{\overset{|}{C}}}}-CH_2-C(CH_3)_2-$$

$$CH_3-\underset{C_2H_5}{\overset{H}{\underset{|}{\overset{|}{C}}}}-(CH_2)_3-C(CH_3)_2-, \text{ etc.}$$

The parent starting monoamine employed in the initial reaction to form the diimino compound can be varied widely depending on the desired diamino compound.

The diamino compounds obtained in the practice of this invention have particular use as catalysts in the preparation of polyphenylene oxides as more described in Hay U.S. Pat. No. 3,306,875, issued Feb. 28, 1967. More particularly, self-condensation products of aromatic compounds containing a hydroxy group directly bonded to an aromatic nucleus can be obtained by a process which comprises reacting these compounds with oxygen in the presence of a tertiary amine-basic cupric salt complex. The tertiary amines obtained in accordance with our process can be used in the catalyst system employed to make these self-condensation products. The polymers obtained by means of the process described in the aforesaid Hay patent because of their excellent physical, chemical and electrical properties have many uses, for instance, in molding powder formulations either alone or mixed with other polymers and other fillers to make motor parts, such as helical or bevel gears, ratchets, impact parts, gaskets, valve seats, etc. They can also be used to prepare molded, calendered or extruded articles, films, coatings, threads, filaments, tapes and the like for use in electrical applications, such as cable terminals, terminal blocks, and as components of dynamoelectric machines that operate at elevated temperatures.

What we claim as new and desire to secure by Letters Patent of the United States is:

1. The process for making diamino compounds of the formula $$\overset{H}{R-N}-CH_2-CH_2-\overset{H}{N-R}$$

which consists essentially of (1) hydrogenating a preformed imino compound of the formula $$R-N=\overset{H}{C}-\overset{H}{C}=N-R$$

in a methanol solvent and in the added presence of a tertiary alkyl mono-amine of the formula R—NH$_2$ which is used to increase the yield of the diamino compound, the tertiary alkyl mono-amine being present in a molar ratio of from 0.2 to 4.0 mols of the latter per mol of the imino compound, where R in the diimino compound and in the mono-amine is the same and is a monovalent alkyl hydrocarbon of from 4 to 10 carbon atoms containing a tertiary $$\underset{\underset{R'}{|}}{\overset{\overset{R'}{|}}{-C-}}$$

group connected directly to the nitrogen atoms of the mono-amine or the imino compound, and where R' is a member of the class consisting of the methyl radical, the ethyl radical, and mixtures thereof, thereby to form the aforesaid diamino compound, and (2) recovering the above-described diamino compound from the reaction mixture.

2. The process for making a diamino compound of the formula $$CH_3-\underset{\underset{CH_3}{|}}{\overset{\overset{CH_3}{|}}{C}}-\overset{H}{N}-CH_2-CH_2-\overset{H}{N}-\underset{\underset{CH_3}{|}}{\overset{\overset{CH_3}{|}}{C}}-CH_3$$

which consists essentially of (1) hydrogenating a performed imino compound of the formula $$CH_3-\underset{\underset{CH_3}{|}}{\overset{\overset{CH_3}{|}}{C}}-N=\overset{H}{C}-\overset{H}{C}=N-\underset{\underset{CH_3}{|}}{\overset{\overset{CH_3}{|}}{C}}-CH_3$$

in the added presence of methanol as a solvent, and in the further presence of t-butylamine, the amine being present in a molar ratio of from 0.5 to 2.0 mols of the latter per mol of the imino compound, and (2) recovering the formed diamino compound from the reaction mixture.

3. The process as in claim 1 wherein the tertiary alkyl mono-amine is 1,1-dimethyl propyl amine and R is the 1,1-dimethyl propyl radical.

4. The process as in claim 1 wherein the tertiary alkyl mon-amine has the formula $$CH_3C(CH_3)_2CH_2-C(CH_3)_2-NH_2$$

and R is the CH$_3$—C(CH$_3$)$_2$CH$_2$—C(CH$_3$)$_2$ radical.

* * * * *